(12) United States Patent
Ricci et al.

(10) Patent No.: US 6,684,412 B2
(45) Date of Patent: Feb. 3, 2004

(54) COMPRESSIVE COMPOSITE ELASTIC STOCKING

(75) Inventors: Stefano Ricci, Rome (IT); Franco Peroschi, Menaggio-Como (IT)

(73) Assignee: Gloria Maglieria Elastica S.r.l., Menaggio-Comp (IT)

( * ) Notice: Subject to any disclaimer, the term of this patent is extended or adjusted under 35 U.S.C. 154(b) by 0 days.

(21) Appl. No.: 10/110,773

(22) PCT Filed: Oct. 8, 2001

(86) PCT No.: PCT/EP01/11602

§ 371 (c)(1),
(2), (4) Date: Jul. 11, 2002

(87) PCT Pub. No.: WO02/34179

PCT Pub. Date: May 2, 2002

(65) Prior Publication Data

US 2002/0172781 A1 Nov. 21, 2002

(30) Foreign Application Priority Data

Oct. 20, 2000 (IT) ..................................... MI2000A2281

(51) Int. Cl.[7] .............................................. A43B 17/00
(52) U.S. Cl. ............................ 2/240; 602/63; 66/178 A
(58) Field of Search ........................... 2/239, 240, 241, 2/242, 409, 61; 602/63; 66/178 A, 178 R, 172 E, 190, 197

(56) References Cited

U.S. PATENT DOCUMENTS

| | | | | |
|---|---|---|---|---|
| 3,386,270 A | * | 6/1968 | Simmons ................... | 66/178 A |
| 3,605,122 A | * | 9/1971 | Myers ......................... | 2/239 |
| 3,828,369 A | * | 8/1974 | Swallow ...................... | 602/63 |
| 4,027,667 A | * | 6/1977 | Swallow et al. ............... | 602/63 |
| 4,172,456 A | | 10/1979 | Zens | |
| 4,180,065 A | * | 12/1979 | Bowen ......................... | 602/63 |
| 4,502,301 A | * | 3/1985 | Swallow et al. .......... | 66/178 A |
| 4,506,392 A | * | 3/1985 | White ........................... | 2/239 |
| 4,561,267 A | * | 12/1985 | Wilkinson et al. ........ | 66/178 A |
| 4,745,917 A | * | 5/1988 | Hasty et al. ................... | 602/63 |
| 5,097,537 A | * | 3/1992 | Ewing ........................... | 2/409 |
| 5,412,957 A | * | 5/1995 | Bradberry et al. ........ | 66/178 A |
| 5,497,513 A | * | 3/1996 | Arabeyre et al. .............. | 2/240 |
| 5,575,013 A | * | 11/1996 | Krack ............................ | 2/239 |
| 5,581,817 A | * | 12/1996 | Hicks ............................ | 2/239 |
| 5,953,759 A | * | 9/1999 | Bozzini ......................... | 2/409 |
| 6,012,177 A | * | 1/2000 | Cortinovis .................... | 2/239 |
| 6,105,173 A | * | 8/2000 | Brown .......................... | 2/239 |
| 6,123,681 A | * | 9/2000 | Brown, III ................... | 602/75 |
| 6,209,141 B1 | * | 4/2001 | Adeli ............................ | 2/239 |
| 6,216,495 B1 | * | 4/2001 | Couzan et al. ............... | 66/183 |
| 6,311,334 B1 | * | 11/2001 | Reinhardt et al. ............ | 2/239 |
| 6,324,698 B1 | * | 12/2001 | Freeman ....................... | 2/239 |
| 6,371,933 B1 | * | 4/2002 | Gardon-Mollard ........... | 602/62 |

FOREIGN PATENT DOCUMENTS

| | | |
|---|---|---|
| EP | 0 553 615 | 8/1993 |
| GB | 295 886 | 8/1928 |

* cited by examiner

*Primary Examiner*—A. Vanatta
*Assistant Examiner*—Alissa L Hoey
(74) *Attorney, Agent, or Firm*—Oblon, Spivak, McClelland, Maier & Neustadt, P.C.

(57) ABSTRACT

A compressive composite elastic stocking which is easier to put on comprising at least two parts (11, 12; 111, 112) suitable for realizing, when applied to a leg (16), a stocking in a single piece with a predetermined degree of compression.

6 Claims, 2 Drawing Sheets

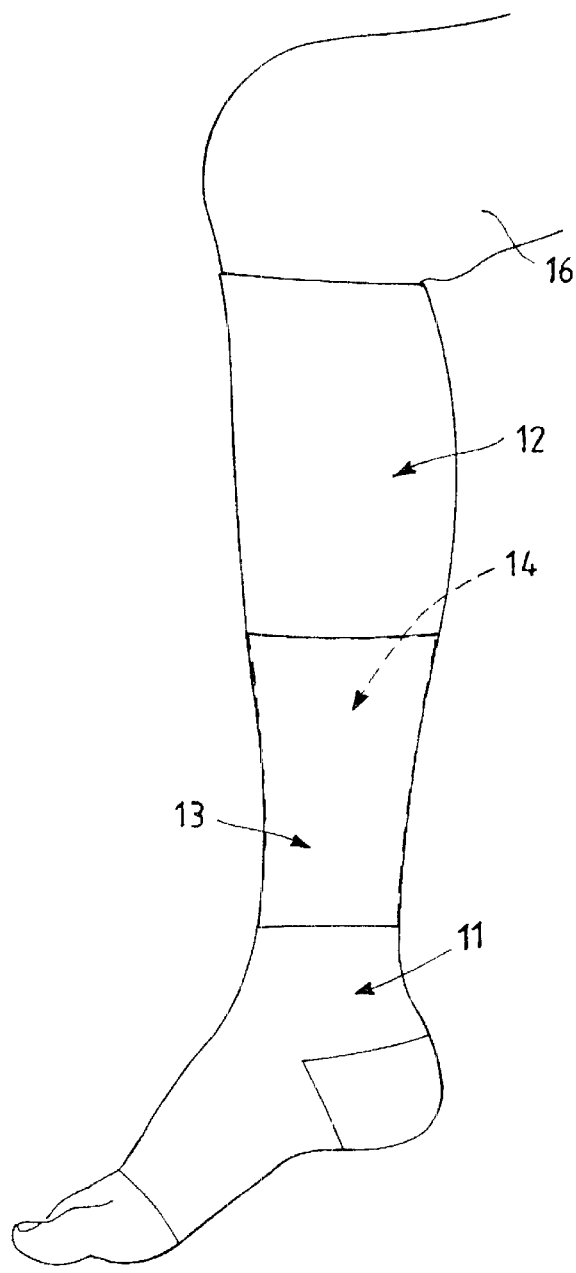
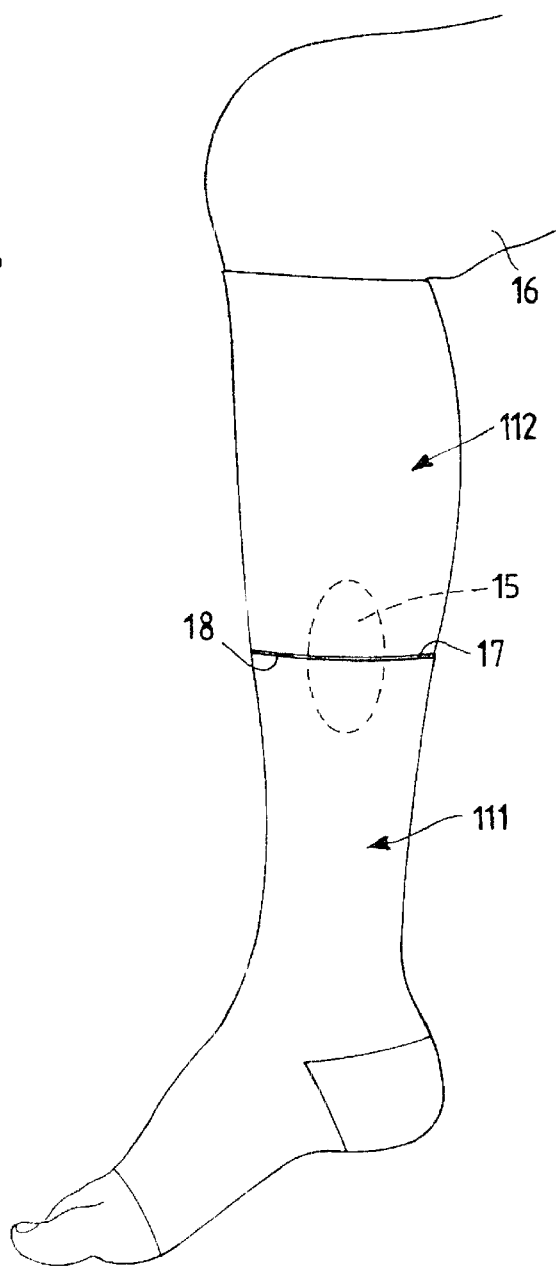

COMPRESSIVE COMPOSITE ELASTIC STOCKING

The present invention refers to an improved compressive composite elastic stocking.

It must be specified that in this description, with the term "stocking" are meant actual hosiery such as stockings, tights, socks, etc., with a closed toe or with an open toe.

Moreover, the term stocking of the "elastic" type indicates stockings, as specified above, with different degrees of compression, for example determined by the greater or lesser presence of elastomeric threads and/or natural rubber, in combination with cotton, polyamide, polyester and other types of fibres.

Actually, these types of elastic stockings are used, in particular, for the treatment of varicose veins, venous insufficiency, thrombophlebitis and other problems related to venous diseases.

The use of this type of stockings is intended, for the most part, for patients of a certain age, who may have some difficulty in applying them to their leg or to part of it. This problem is worsened precisely due to the elasticity of the stocking which, especially if there is high elasticity, requires a certain effort for application, gradually increasing in those users which have little mobility of the spinal column.

A further problem is that relative to the possible presence of ulcerated or inflamed areas of skin to which medication or other treatments need to be applied.

One can imagine, for example, the difficulty of applying a medication with the relative gauze, cotton and other dressings near to a varicose ulcer located in an intermediate area of the lower part of the leg. The elasticity of this type of stocking, if on the one hand is very useful for taking care of and supporting parts which are unhealthy, on the other hand makes it difficult to correctly position both the medication and the relative dressings as well as the stocking due to the pressure inherent to it. Indeed, it is easy to cause the medication to move which thus does not carry out its task correctly and the venous problem persists and can even irreversibly worsen.

In order to try to ease such an operation and to avoid undesired displacements, application aids have been developed which, although easing the manipulation, are not at all practical. Indeed, it must always be considered that for the most part the user has little ease of movement and is not particularly accustomed to using solutions which are complicated and difficult to use.

In light of the problems quoted above an object of the present invention is that of realising compressive elastic stocking which has the easiest possible application or positioning.

A further object is that of allowing, without the use of special and specific aids, the intervention, where necessary, to carry out the medication of ulcers and other unhealthy parts, having a certain guarantee regarding the stable positioning of the medication and of that which is connected to it.

These objects according to the present invention are achieved by realising a compressive composite elastic stocking which is easier to put on as disclosed in claim 1.

Further characteristics are underlined and highlighted in the dependent claims.

The characteristics and advantages of a compressive composite elastic stocking which is easier to put on according to the present invention will become clearer from the following description, given as an example and not for limiting purposes, referring to the attached schematic drawings wherein:

FIG. 2 is a side elevation view of the stocking of FIG. 1 when applied to the lower part of a leg, to realise a knee sock, FIG. 3 is an elevation view of a second embodiment of the stocking according to the invention, applied to the leg.

Figure 1:
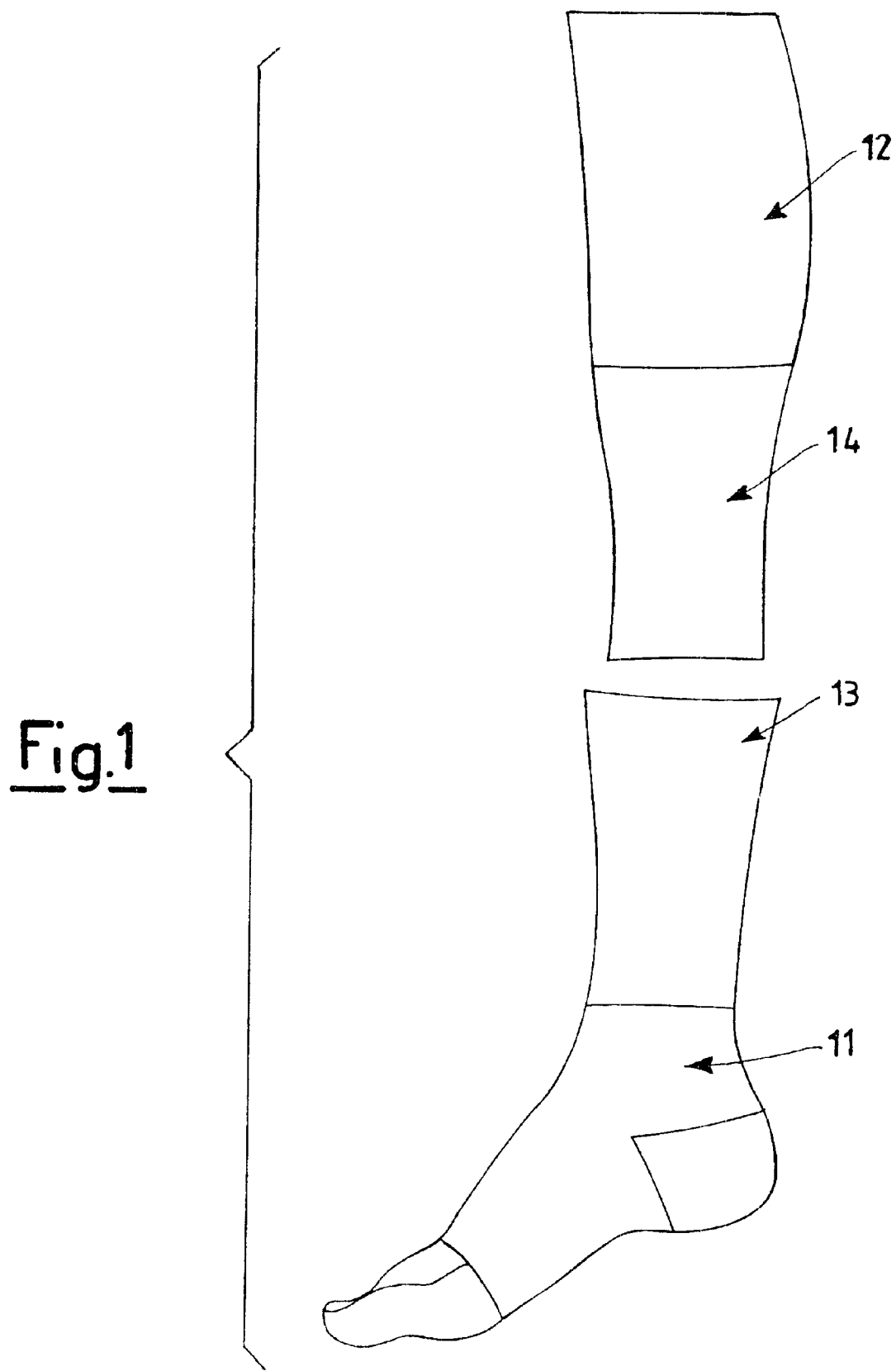
FIG. 1 is an elevation view of a knee sock with its component parts exploded.

With reference to FIGS. 1 and 2, a compressive composite elastic stocking which is easier to put on is shown in a first embodiment thereof in two parts 11 and 12.

A first part 11 is suitable for covering the foot and the lower part of the shin and a second part 12 is suitable for covering the remaining part of the shin up to close to the knee.

Each part 11, 12 has one of its ends 13, 14 facing the other with a degree of compression which is about half of that of the parts 11, 12 constituting the stocking.

These parts 13 and 14, with a lower degree of compression, are intended to be folded on top of each other so as to realise the degree of compression of the stocking. In such a way one manages to recreate a calibrated compression, still with the presence of a break which eases both the application of the stocking and the intervention beneath it.

The division in two parts 11 and 12 of the stocking has substantial advantages with respect to single-piece stocking known up to now, solving the technical problems identified thereof.

Firstly, the application of the parts of the stocking on the leg, particularly for people without good movement and/or of a certain age, who have difficulty in positioning a long single-piece stocking or equally a knee sock, is eased.

Secondly, in the presence of ulcerated or unhealthy areas, which need medication or similar, the division into parts of the stocking makes it easier to apply the medication and the relative dressings, avoiding that they be accidentally removed precisely by the application of the stocking. Indeed, by determining the length of the two parts 11, 12 in function of the ulcerated and injured area, one can provide for the replacement of the medication with the relative dressing without the total removal of the stocking; it could indeed be sufficient to fold over the ends 13 and 14, to replace a "complete medication" 15, indicated with a broken line in FIG. 3, and to reposition only the ends 13 and 14 on top of one another, as in FIG. 2.

Thirdly, whatever the degree of compression, one can still obtain an eased positioning of the stocking.

FIG. 2 shows how the stocking in its two parts 11, 12 is positioned on a leg 16, with overlapping ends 13 and 14 to reform the integrity of the stocking.

FIG. 3 shows a second embodiment of a stocking according to the present invention wherein two parts 111 and 112 are arranged with the end edges 17 and 18 tip to tip to restore the integrity of the stocking along its length on the leg 16.

Also in this case the presence of a break in the stocking, as well as easing the correct positioning, eases the application of a medication or whatever else. With a stocking according to the present invention those aiding elements which were used up to now for the positioning of these elastic stockings, particularly with high degrees of compression are thus not necessary.

The break in the stocking avoids the possible displacement of the medication and an easy replacement of the medication.

In this case, the patient can attend to his medication directly, leaving only the check by the patient's doctor and eliminating, as far as possible, the need for a nursing service which is not always easy to obtain.

In the case of the overlapping ends, the presence of areas with a reduced or halved degree of compression avoids a "snaring" effect which would worsen the conditions of the part of the leg which is unhealthy or being cared for.

The stocking or rather the parts thereof 11, 12 and 111, 112 are realised in various natural, synthetic or artificial fibres, with non-woven primary fabric, in whatever colour, with a suitable diameter, without edges, etc., according to the specific need.

Moreover, it is possible to realise any desired combination on the leg or on a portion of it with parts of the stocking capable of diversified compression.

The end area, i.e. the compression area, can be realised in variable sizes in function of the injury or ulcer, and in function of the application time of the stocking or of a part thereof.

The parts of the stocking can also be used separately on areas of the outside of the leg or even in association with a further supplementary aid, such as an elastic bandage, a knee sock, tights, etc., in relation to the clinical requirements.

The substantial advantages of the present invention which resolves the problems of the prior art are thus clear.

What is claimed is:

1. A compressive composite elastic stocking, comprising:
   a first part having elastic and shaped to be worn on a user's foot;
   a second part configured to be applied to the user's leg separately from the first part, having elastic and shaped to be worn on the user's leg,
   wherein the first part and the second part when worn superposed on the user provide a predetermined uniform compression along the user's leg and foot, and
   wherein a first end of the first part and a second end of the second part individually exert a lower degree of compression, such that when the first part and the second part are superposed at the first end and the second end to form the single piece, the predetermined degree of uniform compression is exerted.

2. The elastic stocking according to claim 1, wherein a second end of the first part and a first end of the second part exert a substantially uniform compression.

3. The elastic stocking according to claim 1, wherein the first part and the second part include at least one of a natural and an artificial fiber.

4. The elastic stocking according to claim 1, wherein the first part and the second part combine to cover the user's entire thigh, calf, and foot.

5. The elastic stocking according to claim 1, wherein the first part and the second part combine to cover the user's calf and foot.

6. The elastic stocking according to claim 1, wherein the lower degree of compression is one half the predetermined degree of uniform compression.

* * * * *